(12) United States Patent
Emrick et al.

(10) Patent No.: US 7,989,544 B2
(45) Date of Patent: Aug. 2, 2011

(54) AMPHIPHILIC POLYMER CAPSULES AND RELATED METHODS OF INTERFACIAL ASSEMBLY

(75) Inventors: Todd S. Emrick, South Deerfield, MA (US); Kurt Breitenkamp, Northampton, MA (US)

(73) Assignee: University of Massachusetts, Boston, MA (US)

( * ) Notice: Subject to any disclaimer, the term of this patent is extended or adjusted under 35 U.S.C. 154(b) by 0 days.

(21) Appl. No.: 12/928,478

(22) Filed: Dec. 13, 2010

(65) Prior Publication Data

US 2011/0091533 A1    Apr. 21, 2011

Related U.S. Application Data

(62) Division of application No. 12/574,482, filed on Oct. 6, 2009, now Pat. No. 7,851,543, which is a division of application No. 10/934,084, filed on Sep. 3, 2004, now Pat. No. 7,598,313.

(60) Provisional application No. 60/500,549, filed on Sep. 5, 2003.

(51) Int. Cl.
 *C08L 27/12* (2006.01)

(52) U.S. Cl. ........ 524/553; 524/800; 524/801; 524/802; 524/804; 524/812; 524/819; 524/821; 524/822; 524/823; 524/824; 524/832; 524/833; 524/845; 524/846; 424/451

(58) Field of Classification Search .................. 524/553, 524/800, 801, 802, 804, 812, 819, 821, 822, 524/823, 824, 832, 833, 845, 846; 424/451
See application file for complete search history.

(56) References Cited

U.S. PATENT DOCUMENTS

| | | | |
|---|---|---|---|
| 4,931,362 A | 6/1990 | Zsifkovits et al. | |
| RE35,717 E | 1/1998 | Nahm | |
| 6,479,592 B2 | 11/2002 | Rheinberger et al. | |
| 6,558,665 B1 | 5/2003 | Cohen et al. | |
| 6,835,394 B1 | 12/2004 | Discher et al. | |
| 7,160,969 B2 | 1/2007 | Piccinelli et al. | |
| 2003/0087985 A1 | 5/2003 | Hubbell et al. | |
| 2003/0125237 A1 | 7/2003 | Kim et al. | |
| 2003/0203991 A1 | 10/2003 | Schottman et al. | |
| 2004/0032038 A1 | 2/2004 | Ali et al. | |
| 2004/0138329 A1 | 7/2004 | Hubbell et al. | |
| 2004/0185107 A1 | 9/2004 | Rubinstein et al. | |
| 2004/0197357 A1 | 10/2004 | Heming et al. | |
| 2004/0208930 A1 | 10/2004 | Yoneda et al. | |
| 2004/0219216 A1 | 11/2004 | Rubinstein et al. | |
| 2004/0228831 A1 | 11/2004 | Belinka et al. | |
| 2004/0234590 A1 | 11/2004 | Mane et al. | |
| 2004/0247675 A1 | 12/2004 | Gruber | |
| 2004/0253184 A1 | 12/2004 | Li et al. | |
| 2004/0266944 A1 | 12/2004 | Wiercinski et al. | |
| 2004/0267354 A1 | 12/2004 | Ringeisen et al. | |
| 2005/0008690 A1 | 1/2005 | Miller | |
| 2005/0019371 A1 | 1/2005 | Anderson et al. | |
| 2005/0019399 A1 | 1/2005 | Fischer et al. | |
| 2005/0019409 A1 | 1/2005 | Edgren et al. | |
| 2006/0058476 A1 | 3/2006 | Piccinelli et al. | |

OTHER PUBLICATIONS

Kurt Breitenkamp, E.A. Novel Polymer Capsules from Amphiphilic Graft Copolymers and Cross-Metathesis. J. Am. Chem. Soc., vol. 125, No. 40, Dec. 9, 2003, pp. 12070-12071, XP002503995.

Mir Mukkaram Ali, E.A. Polymeric Capsules Prepared in Situ Synthesis and Cross-Linking of Amphiphilic Copolymer by Atom Transfer Radical Polymerization. Macromolecules, vol. 36, No. 6, Jan. 3, 2003 pp. 1793-1801 XP002503996.

Ruxandra Gref, E.A. Biodegradable Long-Circulating Polymeric Nanospheres. Science, vol. 263, No. 5153, Mar. 18, 1994 pp. 1600-1603, XP002503997.

Vladimir P. Torchilin. Structure and design of polymeric surfactant-based drug delivery systems. Journal of Controlled Release, vol. 73, No. 2-3, Jun. 15, 2001, pp. 137-172, XP004246457 *p. 144-153*.

Helmut Ringsdorf, E.A. Molekulare Architektur und Funktion von polymeren orientierten Systemen—Modelle fur das Studium von Organisation, Oberflachenerkennung und Dynamik bei Biomembranen. Angew. Chem., vol. 100, No. 1, Jan. 1988, pp. 117-162, XP002503999.

Kurt Breitenkamp, E.A. Novel Amphiphilic Graft Copolymers Prepared by Ring-Opening Metathesis Polymerization of Poly(ethylene glycol)-Substituted Cycootene Macromonomers. Macromolecules, vol. 35 No. 25, Nov. 6, 2002, pp. 9249-9252, XP002504000.

*Primary Examiner* — Bernard Lipman

(74) *Attorney, Agent, or Firm* — Reinhart Boerner Van Deuren s.c.

(57) ABSTRACT

Polymer capsules from amphiphilic graft copolymers comprising reactive, hydrophobic polyolefin backbones, and hydrophilic poly(ethylene glycol) (PEG) grafts are produced by self-assembly of the polymers at the oil-water interface, and crosslinking the assembly with bis-cyclooctene PEG derivatives in conjunction with ring-open metathesis polymerization catalysts. The use of the graft copolymer architecture in capsule synthesis provides significant opportunities to tune both the surface properties, in terms of recognition, and the membrane properties, in terms of mechanical strength, encapsulation, and release.

27 Claims, 4 Drawing Sheets

Figure 2
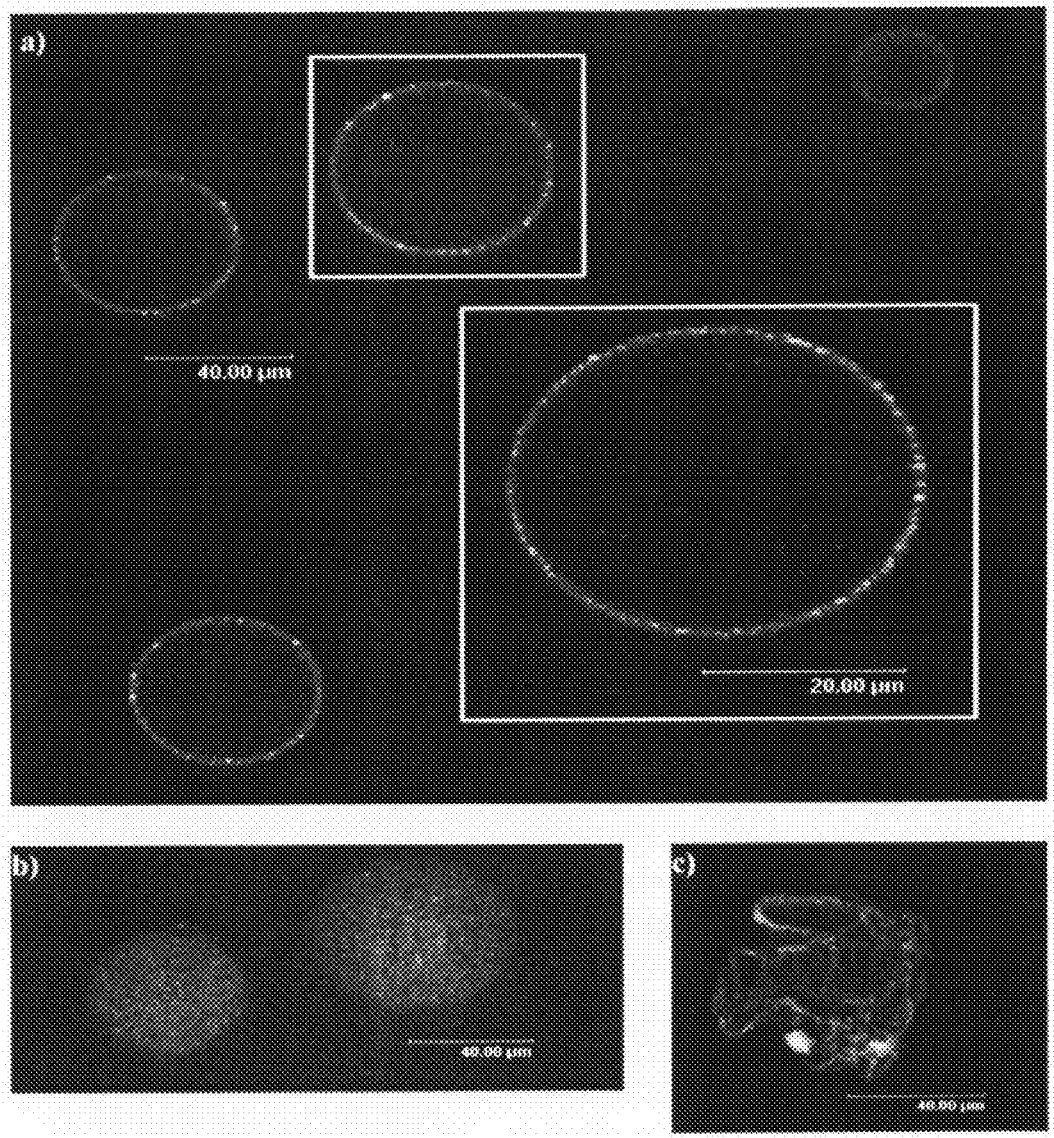
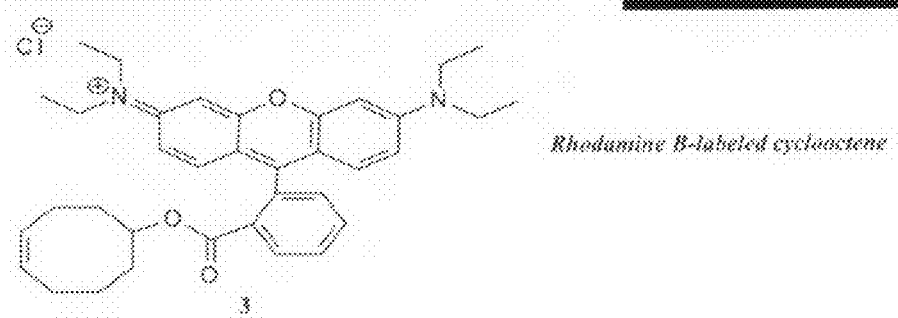
Rhodamine B-labeled cyclooctene

AMPHIPHILIC POLYMER CAPSULES AND RELATED METHODS OF INTERFACIAL ASSEMBLY

This application is a divisional of and claims priority benefit from application Ser. No. 12/574,482 filed Oct. 6, 2009, now issued as U.S. Pat. No. 7,851,543, which was a divisional of and claimed priority benefit from application Ser. No. 10/934,084 filed Sep. 3, 2004 and issued as U.S. Pat. No. 7,598,313 issued on Oct. 6, 2009, which claimed priority benefit from provisional application Ser. No. 60/500,549 filed Sep. 5, 2003, each of which is incorporated herein by reference in its entirety.

The United States Government has certain rights to this invention pursuant to Grant No. CHE0239486 from the National Science Foundation to the University of Massachusetts.

BACKGROUND OF THE INVENTION

Polymer self-assembly is of considerable interest for the preparation of well-defined structures and materials. While polymer materials in solution are most commonly polydisperse random-coils, advances in polymer synthesis, supramolecular assembly, and interfacial segregation have generated polymer-based materials with structural features that possess unprecedented precision. When polymer assemblies contain reactive functionality, opportunities arise for crosslinking, and thus structural solidification, to give materials with wide applicability in both materials science and medicine.

An increased understanding of materials at a system or phase interface offers tremendous opportunities with regard to surfaces, thin films, and nano-structured materials. Amphiphilic polymers are particularly useful for mediation of the oil-water interface, as demonstrated by their rich science and commercial utility as polymer surfactants. Amphiphilic block copolymers are very interesting in this regard, as the range of accessible chemistries and molecular weights, for example in amphiphilic diblock copolymers, leads to polymer assemblies, micelles, and vesicles of considerable interest for encapsulation and controlled release.

The synthesis of amphiphilic graft copolymers has been the subject of on-going research, as the graft copolymer structure can be used to integrate into the polymer backbone functionality for subsequent chemical modification. Particular interest has been afforded copolymers of hydrophobic polyolefin backbones with covalently bound hydrophilic poly(ethylene glycol) (PEG) pendant chains, the preparation of which can be achieved by ring-opening metathesis copolymerization of cyclooctene and PEG-substituted cyclooctene macromonomers. The resulting PEGylated polycyclooctene copolymers can be designed or tuned as desired in terms of their backbone composition and graft molecular weight. In addition, a variety of grafted functionality and linker chemistry is accessible. However, the study of such compounds has not been extended to polymeric architectures and the interfacial assemblies thereof.

BRIEF DESCRIPTION OF THE DRAWINGS

FIG. 2. (a) Confocal laser scanning micrograph cross-section of microcapsules using graft copolymer 1 with Mn ca. 55K; the fluorescence arises from integration of cyclic olefin 3 into the graft copolymer; (b) projection image showing accumulated cross-sections of two capsules; (c) a collapsed capsule membrane after introduction of ethanol.

SUMMARY OF THE INVENTION

Figure 1:
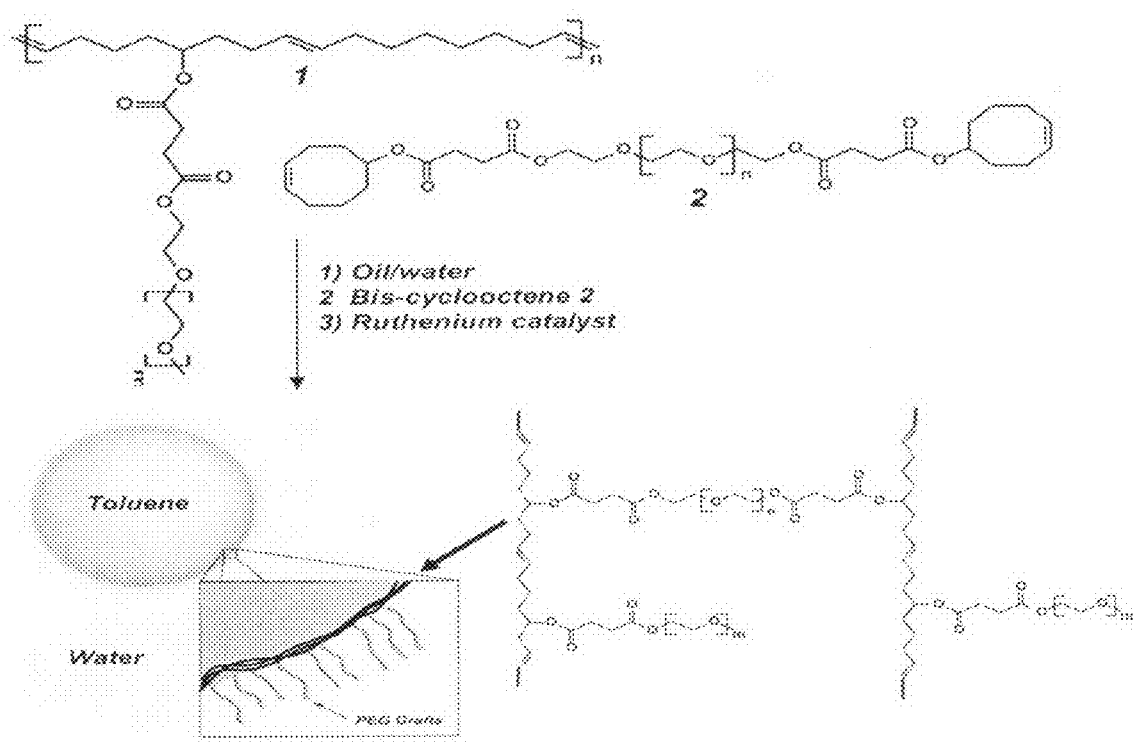
FIG. 1. Schematic representation of interfacial activity of PEGylated poly(cyclooctene), and the bis-cyclooctene PEG used for crosslinking by ring-opening cross-metathesis.

In light of the foregoing, it is an object of the present invention to provide various graft copolymers and/or related architectures and methods of their production and/or assembly, thereby overcoming various concerns of the prior art, including those outlined above. It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide, contrary to the prior art, a copolymer compound with grafted functionality interactive with one or more phases of a multi-phase environment.

It can be another object of the present invention to provide, in conjunction with the preceding, a graft copolymer with a range of pendant polymeric components, the identity of which is limited only by synthetic technique and desired phase interaction.

It can be another object of the present invention to provide, in conjunction with the preceding and contrary to the prior art, a graft copolymer for interfacial self-assembly and/or encapsulation of a phase component and/or material dispersed or otherwise contained therein.

Other objects, features, benefits and advantages of the present invention will be apparent from this summary and its descriptions of various embodiments, and will be readily apparent to those skilled in the art having knowledge of various polymerization, encapsulation and/or assembly techniques. Such objects, features, benefits and advantages will be apparent from the above as taken into conjunction with the accompanying examples, data, figures and all reasonable inferences to be drawn therefrom.

In part, the present invention is a method of using a graft copolymer for interfacial assembly and/or encapsulation. Such a method comprises (1) providing a mixture of a first fluid phase/component and a second fluid phase/component at least partially immiscible in the first phase/component; and (2) preparing a graft copolymer with polymerization of one or more monomeric components introduced to the mixture or as provided with a phase/component of the mixture. As demonstrated below, a graft copolymer can interfacially assemble to provide a three-dimensional molecular capsule or structure about or encapsulating one of the phase/components.

In certain embodiments, as illustrated below, the graft copolymer comprises an aliphatic backbone component and one or more components pendant thereto with a linker moiety. Likewise, in certain embodiments, the aliphatic component can be polyolefinic or comprise one or more unsaturated bonds. The pendant component(s) can also be polymeric, linked to the backbone component with a moiety or a combination of moieties more or less stable under hydrolytic or cleavage conditions. Structure and/or composition of the backbone and pendant components can be varied by design or for a particular end use application. For instance, the backbone component can be varied by length, molecular weight and/or degree of unsaturation for a particular phase interaction or association. Likewise, one or more pendant components can vary by molecular weight and functionality. Illustrating the latter, a pendant poly(alkylene oxide) component (e.g., PEG or a propylene analog) is amphiphilic, the effect of which in a given fluid mixture can be modified by component length or number of repeating units, molecular weight or end group functionality.

Without limitation, an especially useful polymer useful with this invention can be prepared as described below by the ring-opening metathesis copolymerization of cyclooctene and PEG-substituted cyclooctene macromonomers. Nonetheless, various other graft copolymers can be prepared from a range of other cycloalkenes (e.g., cyclopentene and cycloheptene) or bridged cycloalkenes (e.g., norbornene), each of which can be optionally substituted as would be known to those skilled in the art, and the corresponding poly(alkylene oxide) or PEG-substituted cycloalkene macromonomers. Without limitation, reference is made to example 3. Such cycloalkenes, macromonomers and precursors thereof are limited only by their compatibility with the catalytic system utilized herewith. Accordingly, graft copolymers can also comprise other pendant components including but not limited to oligopeptides and hydrocarbons linked to the aliphatic backbone component by a more hydrolytically-stable group, such as an ether, amide, or less hydrolytically stable group, such as an ester. As shown below, such pendant components and the linker moieties are available from the corresponding cyclic olefin/cycloalkene derivatives. Without limitation, reference is made to examples 1, 4 and 9.

In preferred embodiments, such a method of interfacial assembly and/or encapsulation further comprises crosslinking the assembled graft copolymers to further develop or modify the interfacial assembly and resulting architecture. In certain such embodiments, crosslinking can be achieved upon introduction of the graft copolymer or subsequent thereto, in conjunction with use of the ring-opening cross-metathesis catalyst of the type described herein. In certain such embodiments, crosslinking can be achieved with a bis-cycloalkene component corresponding to the backbone component and/or the pendant component linked thereto. Without limitation, reference is made to example 11. Alternatively, a reactive pendant graft component can be used to crosslink the graft copolymers. For example, pendant methacrylate groups can crosslink copolymers under appropriate photochemical conditions. See examples 14 and 16.

The interfacial assembly and encapsulation of this invention can be considered as relating to polymer interactions with or as introduced to a fluid component mixture in the context of polymeric assembly. Accordingly, the present invention can also be directed to a system for polymeric assembly. Such a system comprises (1) a first fluid phase component; (2) a second fluid phase component at least partially immiscible with the first component; (3) a polymer comprising an aliphatic component with at least one substituent pendent thereto, wherein one of the phase components is interactive with the aliphatic polymeric component and the other phase component is interactive with the substituent. Such a substituent can comprise any of the pendent components mentioned above or as described elsewhere herein. Regardless, in certain embodiments, at least one such substituent is amphiphilic. Without limitation, such a substituent can comprise a poly(alkylene oxide) moiety, such as that derived via reaction with ethylene oxide or propylene oxide. Poly(alkylene oxide) moieties can also be used to cross-link the aforementioned aliphatic components, whether such linkages are effected by ether, ester, amide or other linkage moieties. One such fluid phase/component can be aqueous, protic and/or polar, with a second phase/component at least partially immiscible therewith. Choice of phase/components and polymer, as described above, can provide an assembled polymer architecture for encapsulated delivery of a material soluble, dispersed, partitioned or otherwise contained in one of the phase/components, upon removal of one or both fluid phases.

As demonstrated herein, 3-dimensional, capsule structures have been prepared from PEGylated polyolefins using both oil-in-water systems (i.e., an oil or water-immiscible phase inside the polymeric capsule in a water-based system), as well as in water-in-oil systems. Accordingly, any oil or non-aqueous soluble material (e.g., therapeutic, analytic, diagnostic agent, etc.) can be encapsulated in an oil-in-water system, and any water-soluble material can be encapsulated in a water-in-oil system. Accordingly, the present invention can be used to encapsulate hydrophobic pharmaceutical molecules, as well as hydrophilic materials, or to encapsulate hydrophilic materials in the inverse case. Without limitation, reference is made to examples 16-18.

As mentioned above, the polymer backbone component can be used to effect various structural properties of the resulting architecture, including crosslink density and, thus, permeability and release. Such parameters can be controlled by the amount and type of crosslinker component employed. Further control can be afforded by varying the degree of unsaturation in the backbone component. For instance, the PEGylated poly(cyclooctenes) prepared herein provide one double bond per 8 carbon atoms, as a result of the metathesis copolymerization employed. Such a polymer can be hydrogenated completely to provide polyethylene-graft-PEG, or hydrogenated partially give an adjustable degree of unsaturation remaining along the backbone component. Increased levels of unsaturation, upon assembly at an oil-water interface, will afford a corresponding decrease in crosslink density (given the catalytic system employed) and further opportunity to design or control permeability and release.

The cross-linking chemistry on the graft copolymers can be performed such that crosslinks with hydrolytically stable connectivities are formed (e.g., with ether or amide linkages) or relatively hydrolytically unstable crosslinks are formed (e.g., with ester linkages). Polymeric materials of this invention with more stable crosslinkage can afford longer carrier lifetimes, while those less stable are subject to degradation. Importantly, combinations of hydrolytically stable and hydrolytically unstable crosslinkers can be integrated into the same capsule structure in order to refine capsule permeability, release and rupture profiles. Without limitation, reference is made to examples 4, 11 and 14.

As a related consideration, the composition and structure of the graft polymers of this invention can provide a capability for release from both capsule periphery and interior. For example, hydrolysis and/or cleavage of a pendant component from the polymeric component can change the permeability of the assembled polymeric structure and contribute to the effective release of an encapsulated material. Where the pendant component and the encapsulated material both provide end-use function, such a dual or multiple release can be used to enhance desired therapeutic performance or effect.

In accordance with the preceding, the present invention also provides a diverse class of graft copolymers comprising a backbone component and one or more components pendant thereto with a linker moiety. Such copolymers can be crosslinked with components of the sort described herein. Copolymerization, with optional crosslinking, in a suitable bi-phasic system affords interfacial assembly and provides a 3-dimensional structure or configuration of such compounds. Incorporation of a material or component into one or both system phases, with copolymerization, provides a composite or composition comprising the graft copolymer structure/configuration and a deliverable/releasable material/phase component.

As mentioned above and indicative of the broader compositional and method-related aspects of this invention, the assemblies and capsule formation of this invention can be illustrated with PEGylated polyolefins at the oil-water interface, using graft copolymers that contain, for example, in one embodiment an average of one PEG chain per sixteen carbon atoms of the backbone. The combination of interfacial activity and backbone reactivity of the copolymers leave them amenable to capsule formation. FIG. 1 depicts segregation to an oil-water interface to generate capsules with crosslinked membranes. Indeed, a number of chemistries are accessible on the unsaturated backbone. Ring-opening cross-metathesis chemistry, an extremely useful methodology in small molecule synthesis, was used to generate the desired crosslinking, as this can be performed under mild conditions without disruption of the initial assembly. Samples of bis-cyclooctenyl PEG were prepared for this crosslinking chemistry, by reaction of two equivalents of carboxylic acid functionalized cyclooctene with α,ω-PEG-diol under carbodiimide coupling conditions. These difunctional molecules are, like the graft copolymers, interfacially active, and upon addition of ruthenium benzylidene catalyst react with the polymer assembly by ring-opening cross metathesis.

With reference to the following examples, such polyolefin-graft-PEG capsules can be produced by dissolving graft copolymer 1 of a range of molecular weights (Mn from about 15-about 200 K, with a polydispersity index (PDI) of 1.8) and crosslinker in toluene, adding Grubbs' Generation II catalyst21 to the mixture, and transferring aliquots of this mixture into water. The heterogeneous mixture is shaken for 15 minutes to produce crosslinked capsules that swell in both water and organic solvents, owing to their amphiphilic nature, and are elastomeric as a result of the crosslinked membrane. The capsule density is tunable by choice of organic solvent: e.g., toluene-filled capsules float on water, while capsules filled with higher density solvents (i.e. trichlorobenzene) stand on the bottom of the flask.

Figure 3:
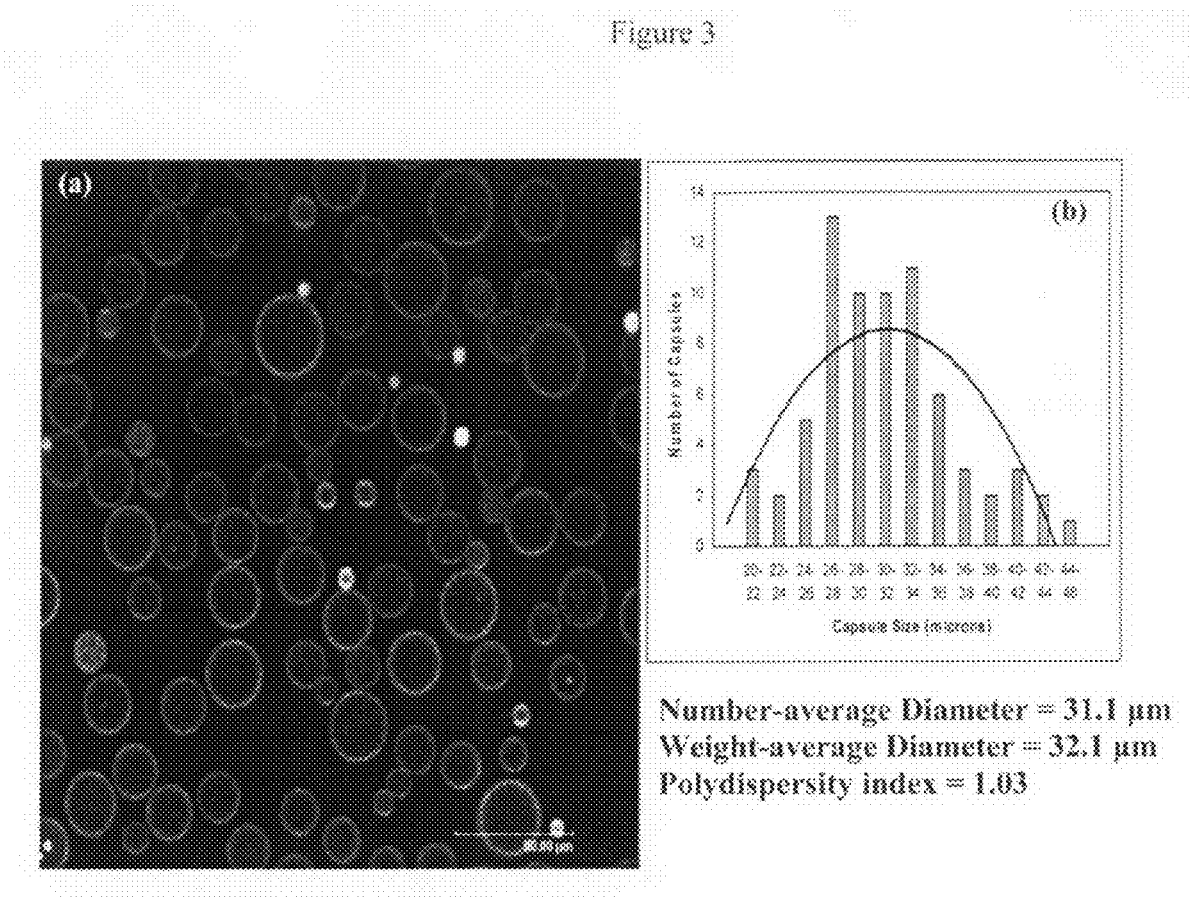
FIG. 3. (a) Confocal laser scanning micrograph cross-section of crosslinked microcapsules using graft copolymer 1 with Mn ca. 80K; the small dark circles represent capsules outside the focal plane and were not included in the analysis, (b) Statistical analysis of FIG. 3a plotting capsule diameter versus capsule number, using 68 capsules in the calculation.

Fluorescence confocal microscopy (Leica inverted confocal microscope) was used to visualize the segregation of these polymers to the oil-water interface. Only a very faint contrast at the interface was observed on the as-prepared copolymers due to their lack of fluorescence emission. Accordingly, a fluorescent cyclooctene derivative was prepared through esterification of 5-hydroxycyclooctene with rhodamine B (Compound 3 in FIG. 2), with the monomer integrated into the amphiphilic graft copolymer by copolymerization with cyclooctene and the pegylated cyclooctene macromonomer. See examples 7 and 8. The functional group tolerance of the catalyst proved very valuable for the preparation of this fluorescent polyolefin. Confocal images of the fluorescent amphiphilic graft copolymer in oil-in-water biphasic systems (FIG. 2a) reveals a strong preference of the graft copolymer for the interface, as indicated by the emission at 556 nm at the equator of an oil droplet in water. The capsules can be adjusted in size, (e.g., from about 40 microns down to about 500 nm) depending on assembly conditions, and can be optimized in terms of size dispersity. (Reference is made to FIGS. 3a-b.) The capsules are hollow, and can be filled with reagents and materials of appropriate solubility.

A three-dimensional reconstruction fluorescence confocal micrograph cross sections of the capsules is illustrated in the digital image of FIG. 2b, to demonstrate their spherical nature and complete coverage by the polymer. FIG. 2c confirms the effective crosslinking of the graft copolymer by replacing the two-phase oil/water mixture with the mutually good solvent ethanol. Under such conditions, the capsules do not dissolve away. Rather, the collapsed crosslinked membrane can be isolated and visualized clearly. Preliminary atomic force microscopy (AFM) images, performed on capsules dried on silicon substrates, evidence the presence of a thin polymer membrane on the droplet surface.

The polymer capsules described herein are useful in a range of encapsulation and release applications, and benefit from the graft copolymer architecture used in their synthesis. The same architecture provides significant opportunity for integration of a large number and diverse range of functional groups onto the capsule surface, such groups limited only by their amphiphilicity and their ability to promote, or not deter, interfacial assembly. The PEGylated polycyclootene capsules are believed biocompatible given the presence of the PEG grafts. Such properties can be modified and enhanced through the integration of oligopeptides into these structures, further affecting membrane morphology and permeability.

EXAMPLES OF THE INVENTION

The following non-limiting examples and data illustrate various aspects and features relating to the compounds, compositions and/or methods of the present invention, including the assembly of graft polymeric structures having various pendant phase-interactive functionalities, as are available through the synthetic methodology described herein. In comparison with the prior art, the present compounds, compositions and/or methods provide results and the data which are surprising, unexpected and contrary to the prior art. While the utility of this invention is illustrated through the use of several polymeric compounds and molecular components, moieties and/or functionalities used therewith, it will be understood by those skilled in the art that comparable results are obtainable with various other compounds and compositions, as are commensurate with the scope of this invention.

Instrumentation. NMR spectra were collected on a Brüker DPX 300 spectrometer (referenced to $CDCl_3$): $^1H$ at 300 MHz and $^{13}C$ at 75 MHz. UV data was obtained using a Hitachi U-3010 spectrophotometer at a scan rate of 60 nm/mi. Molecular weights and polydispersity indices were estimated using gel permeation chromatography in DMF (0.01 M LiCl, 0.5 mL/min) and referenced against linear polystyrene standards. The system utilized three-columns (Polymer Laboratories 300×7.5 mm, 2 Mixed-D, 50 Å) and a refractive index detector (HP 1047A). Confocal images were obtained using an inverted microscope with TCS SP2 confocal system (Leica). Atomic force microscopy (AFM) images were obtained using a Digital Instruments Dimension 3100 atomic force microscope, Electrospray Ionization (ESI) mass spectroscopy was performed on a Brüker Esquire~LC instrument. Matrix assisted laser desorption/ionization mass spectroscopy was performed on a Brüker Reflex III.

Materials. Cyclooctene, cyclooctadiene, succinic anhydride (99%), and lithium aluminum hydride were purchased from Alfa Aesar. m-Chloroperoxybenzoic acid (MCPBA) (77%), 4-dimethylaminopyridine (DMAP) (99%), 1,3-dicyclohexylcarbodiimide (DCC) (99%), polyethylene glycol (MW ca. 2000), Rhodamine B (90%), and dodecyl vinyl ether (99%) were purchased from Aldrich. 1,3-bis-(2,4,6-trimethylphenyl)-2-(imidazolidinylidene)dichloro(phenylmethylene)(tricyclohexylphosphine)ruthenium was purchased from Strem Chemical.

Example 1a

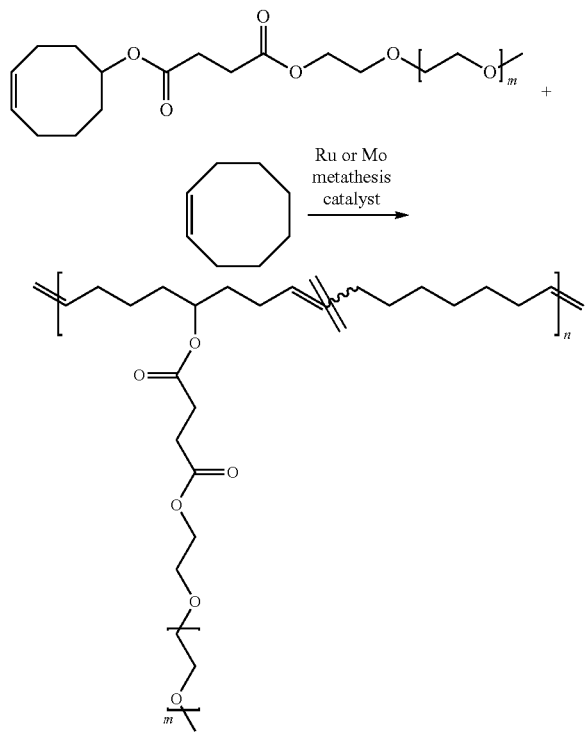

Copolymerization of macromonomer and cyclooctene for synthesis of copolymer 1. 0.50 g (0.52 mmol) of the PEGylated macromonomer (prepared as in Example 2 with equimolar amounts of cyclooctene succinic acid ester and PEG) was weighed into a small tube and degassed under vacuum while stirring at 45° C. 58 mg (0.52 mmol) of cyclooctene was injected into the vessel under $N_{2(g)}$. 3.52 mg (4.14 μmol) of Grubb's Generation II catalyst was weighed into a small vial, degassed, and diluted with 1.04 mL of dry dichloromethane under $N_{2(g)}$. The catalyst solution was introduced by syringe, and the mixture was stirred at 45° C. Upon vitrification, the reaction was terminated using ethyl vinyl ether, and a small amount of $CH_2Cl_2$ (~1 mL) was added to improve stirring. The contents were then precipitated into cold hexane, filtered, and dried under vacuum to yield 0.42 g (84%) of copolymer 1. $^1$H NMR (CDCl$_3$) δ 5.34 (br, olefin 2H), 4.86 (br s, 1H), 4.22 (t, 2H), 3.5-3.7 (complex, br m), 3.36 (s, 3H), 2.61 (br m, 4H), 2.32 (br s), 1.94 (br s), 1.50 (br s), 1.26 ppm (br s); $^{13}$C NMR (CDCl$_3$) δ 172.7 (ester), 172.3 (ester), 130.0, 130.8, 129.3, 74.7, 72.3, 70.9, 69.4, 64.2, 59.4, 34.4, 33.0, 30.0, 29.7, 29.5, 28.8, 25.6 ppm. IR (NaCl plate) 2922, 2867, 1733 (ester), 1456, 1349, 1300, 1250, 1111, 1040, 968, 860 cm$^{-1}$. GPC (DMF w/0.01% LiCl vs. linear polystyrene standards) $M_n$=330,000 g/mol, $M_w$=515,000 g/mol, PDI=1.56. Regardless of monomer identity or choice of catalyst, polymerization enroute to the assemblies of this invention can be effected as described above and in several of the following examples.

Example 1b

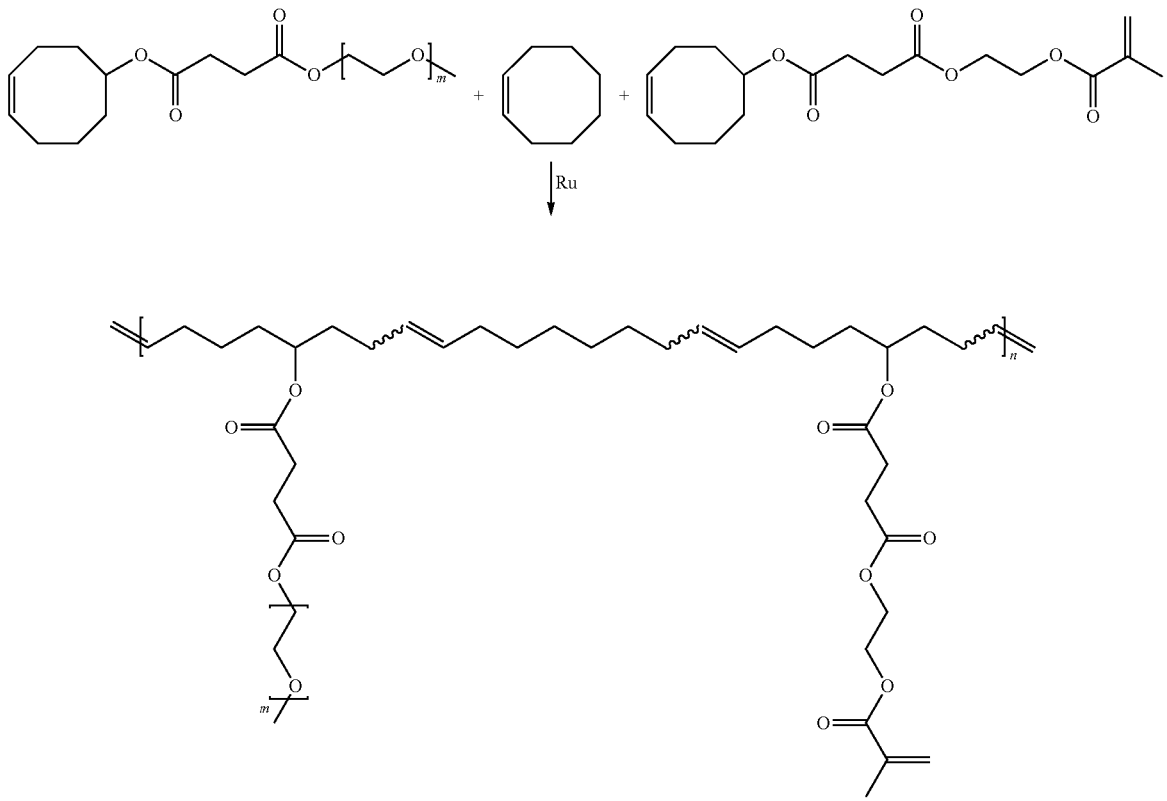

Alternatively, a methacrylate monomer (see ex. 15) can also be used, with encapsulation possible as provided in example 16. PEG 750 (m~16) macromonomer (0.50 g, 0.53 mmol), cyclooctene (0.05 g, 0.43 mmol), and cyclooctene methacrylate (0.04 g, 0.11 mmol) were combined in a reaction tube. 0.13 mL of a 0.04 M 1-hexene solution in dichloromethane was added to the reaction followed by 0.35 mL of dry dichloromethane. In a separate vial, 1.8 mg Grubbs' Generation III catalyst was diluted with 0.2 mL dry dichloromethane. Both the reaction mixture and catalyst solution were subjected to two freeze/pump/thaw cycles followed by addition of the catalyst solution to the reaction mixture. The mixture was stirred at 40° C. until vitrification (3 min). Approximately 1 mL of dodecyl vinyl ether was added to terminate the polymerization and dichloromethane was added to dilute the polymer solution. The product was precipitated into cold hexane, isolated, and dried under vacuum to yield 0.38 g (64%) of polymer. $^1$H NMR (CDCl$_3$) δ 6.12 (s), 5.59 (s), 5.36 (br m), 4.87 (m), 4.33 (s), 4.23 (m), 3.37-3.70 (br m), 3.37 (s), 2.64 (br m), 1.94, (br m), 1.63 (br m), 1.25 (br m); GPC (CHCl$_3$, relative to polystyrene standards) $M_n$ 20,700 Da, $M_w$ 42,200 Da, PDI 2.04.

Example 2 merization with, cyclooctene. These cyclic olefins include but are not limited to substituted and unsubstituted versions of high-strain cyclic olefins such as cyclobutene, norbornene, norbornadiene, oxanorbornene, and dicyclopentadiene, as well as low-strain cyclic olefins such as cyclopentene, cycloheptene, and cyclooctadiene. Such cyclic olefins or cycloalkenes can be used, in accordance with the procedures of examples 1 and 2, to prepare analogous PEGylated macromonomers, graft copolymers and crosslinking compounds.

Example 4

With reference to the macromonomer of example 1, a variety of covalent linkages can be used for attachment of pendant moieties to the polyolefin backbone. The advantage to diversity in linker functionality lies in the ability to tune hydrolysis rates, and in turn control release of encapsulants/agents from the capsule. Macromonomers and resulting copolymers can be prepared with ester, ether, and amide linkages (with appropriate cyclic olefin derivatives and subsequent reaction with PEG) and extended to include urethane, urea, imide, and acrylate linkages.

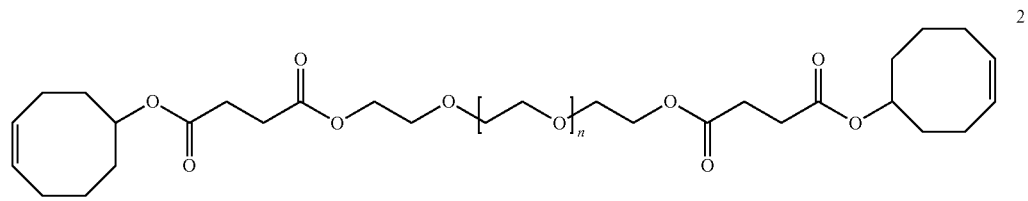

2

Synthesis of bis-cyclooctene PEG (2). Succinic acid monocyclooct-4-enyl ester (2.55 g, 11.2 mmol), poly(ethylene glycol) (9.00 g, 4.50 mmol) of ca. 2000 a.m.u., and N,N-dimethylaminopyridine (110 mg, 0.90 mmol) were stirred in dry CH$_2$Cl$_2$ (30 mL) under N$_{2(g)}$. In a separate flask, dicyclohexylcarbodiimide (1.96 g, 9.50 mmol) was dissolved with pyridine (1.18 g, 14.9 mmol) and CH$_2$Cl$_2$ (10 mL); this solution was added by syringe to the reaction mixture and stirred for 24 hours at room temperature under N$_{2(g)}$. The mixture was washed with 1 M HCl$_{aq}$ and concentrated. The product was dissolved in water and extracted with hexane/ethyl acetate. The aqueous phase was extracted with CH$_2$Cl$_2$, dried over MgSO$_4$, concentrated, and dried under vacuum overnight to yield the bis-cyclooctene PEG product (10.3 g, 95%) as a white, waxy solid; $^1$H NMR (CDCl$_3$) δ 5.65 (m, 4H), 4.83 (m, 2H), 4.22 (t, 4H), 3.5-3.7 (complex, br m, ~180H), 2.55-2.67 (m, 8H), 1.57-2.4 (m, 20H) ppm; $^{13}$C NMR (CDCl$_3$) δ 172.4 (ester), 171.6 (ester), 129.8, 129.6, 76.8, 72.0, 70.6, 69.1, 63.9, 59.1, 33.7, 33.6, 29.5, 29.2, 25.6, 24.9, 22.3 ppm; MALDI Peak MW m/z=2393.7 g/mol. Regardless of cycloalkene, linear moiety (e.g., ether, ester, amide, etc.) cross-linking component, coupling enroute to the bis-cycloalkenes described herein can be effected as described above or using straight-forward modifications of such techniques, depending upon choice of starting materials.

Example 3

In addition to cyclooctene, other cyclic olefins can be integrated into the copolymer structure in place of, or in copoly- Example 5a

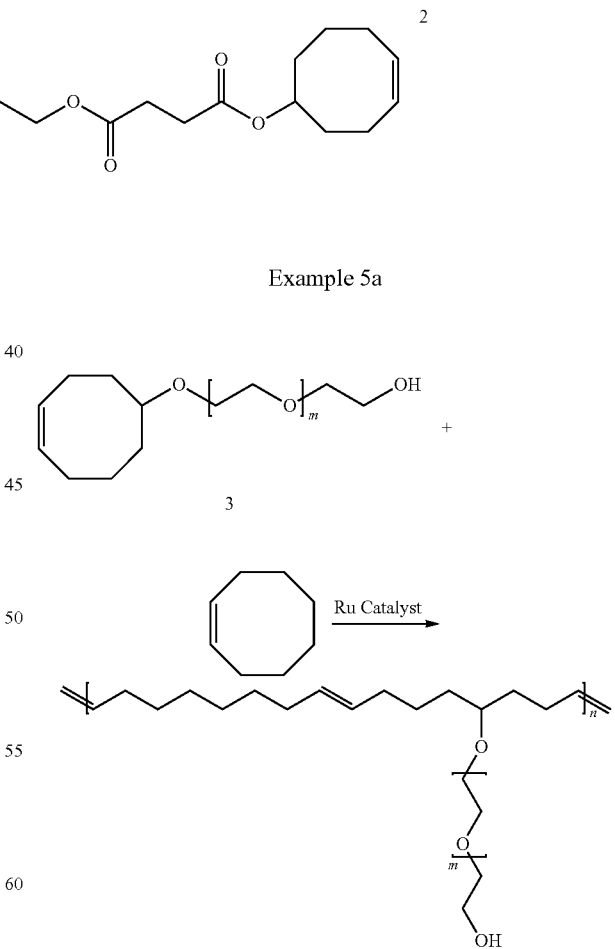

PEGylated macromonomer 3 comprises an ether linkage to connect the PEG chain to the cyclooctene moiety, and can be homopolymerized, or copolymerized with unsubstituted cyclooctene to give the PEGylated amphiphilic graft copolymer 4. The synthetic procedure for synthesizing graft copolymer 4 is analogous to the procedure of Example 1. The ether linkage of polymer 4 significantly enhances the hydrolytic stability of the graft copolymer relative to the ester-linkage illustrated in Example 1.

More specifically, PEG 1300 (m~30) macromonomer (1.0 g, 0.7 mmol) and cyclooctene (0.2 g, 1.6 mmol) were combined in a reaction tube. 0.46 mL of a 0.05 M 1-hexene solution in dichloromethane was added to the reaction followed, by 0.5 mL of dry dichloromethane. In a separate vial, 2.0 mg Grubbs' Generation II catalyst was diluted with 0.2 mL dry dichloromethane. Both the reaction mixture and catalyst solution were subjected to two freeze/pump/thaw cycles followed by addition of the catalyst solution to the reaction mixture. The mixture was stirred at 40° C. until vitrification (5 min). Approximately 1 mL of ethyl vinyl ether was added to terminate the polymerization and dichloromethane was added to dilute the polymer solution. The product was precipitated into cold hexane, isolated, and dried under vacuum to yield 0.91 g (77%) of polymer. $^1$H NMR (CDCl$_3$) δ 5.36 (m), 3.37-3.97 (br m), 3.24 (br m), 2.43 (br s), 1.94, (br m), 1.27-1.53 (br m); $^{13}$C NMR (CDCl$_3$) δ 130.2, 72.6, 70.6, 70.3, 61.7, 32.6, 29.6, 29.1; ATR-FTIR 2921, 2852, 1468, 1344, 1281, 1242, 1104, 963, 842 cm$^{-1}$.

Example 5b

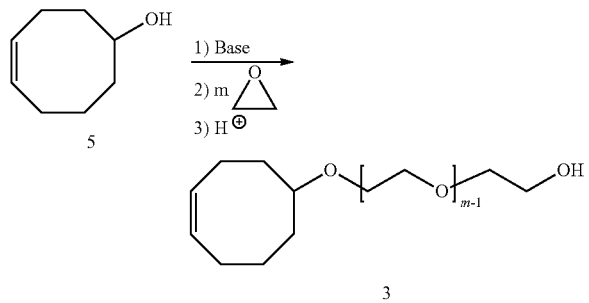

The synthesis of macromonomer 3 (of Example 5a) permits a wide range in variation of the PEG graft length (m is the number of PEG repeat units) by polymerization of ethylene oxide from the alkoxide of 5-hydroxycyclooctene 3. Varying the PEG chain length impacts a number of properties in the resulting copolymer 4, including relative hydrophilicity, and backbone vs. pendant graft crystallization. In addition, when considering the formation of capsules from these graft copolymers, it is found that the capsule size and stability can be effectively tuned by varying the length and number of the PEG grafts. In general, increased number and length of the PEG grafts results in decreased capsule size and increased stability before crosslinking. Generally, the use of fewer PEG grafts, and those of lower molecular weight, give capsules with significantly shorter shelf lives. Variation of these and other aspects of polymer architecture and composition can provide capsules ranging from about 5 to about 80 µm in diameter.

Example 5c

More specifically, PEGylated monomer 3 can be prepared as follows. In a flame dried air-free flask, 6.36 mL (6.36 mmol) of a 1.0 M 5-hydroxycyclooctene solution in tetrahydrofuran (THF) was added to 200 mL of dry THF. The solution was titrated with a 0.5 M diphenylmethyl potassium solution in THF until a slight yellow end-point was observed (approx. 13.1 mL (6.55 mmol)). The cyclooctene alkoxide solution was allowed to stir an additional 30 minutes at room temperature followed by cooling in an ice/salt water bath. Ethylene oxide (14.0 mL, 317.9 mmol) was condensed at −78° C., slowly warmed to room temperature, and transferred to the cooled cyclooctene alkoxide solution under inert atmosphere. The reaction mixture was sealed and allowed to stir at room temperature for 16 hr. The macromonomer was purified by removing THF, dissolving the product in water, and washing with diethyl ether. The product was removed from the aqueous portion by extraction with chloroform (3×), and the combined organic fractions were combined, dried over magnesium sulfate, and concentrated to a viscous liquid. The concentrate was dissolved in a minimal amount of ethyl acetate and precipitated into a hexane/diethyl ether mixture. The white powder was isolated and dried under vacuum to yield 10.4 g (74% yield) of pure macromonomer. $^1$H NMR (CDCl$_3$) δ 5.62 (m, 2H), 3.28-3.84 (complex, br m, 228H), 2.54 (br s, 1H), 1.28-2.36 (complex br m, 11H); $^{13}$C NMR (CDCl$_3$) δ 130.2, 129.6, 81.1, 72.7, 71.0, 70.7, 70.4, 67.8, 61.8, 34.2, 33.5, 25.9, 25.8, 22.8; ATR-FTIR 3491, 2882, 1467, 1359, 1341, 1280, 1242, 1100, 1060, 959, 841, 725 cm$^{-1}$; GPC (THF, relative to polystyrene standards) M$_n$ 2759 Da, M$_w$ 2709 Da, PDI 1.11.

Example 6

As shown below, an amide-linked macromonomer can be prepared by functionalization of cyclooctene carboxylic acid 6 with mPEG amine 7 to give amide-linked macromonomer 8. The length of PEG-chain can be varied, with this monomer and with others herein, without limitation, over a wide range of repeat units, with n in some embodiments ranging from about 2 to about 120 or greater.

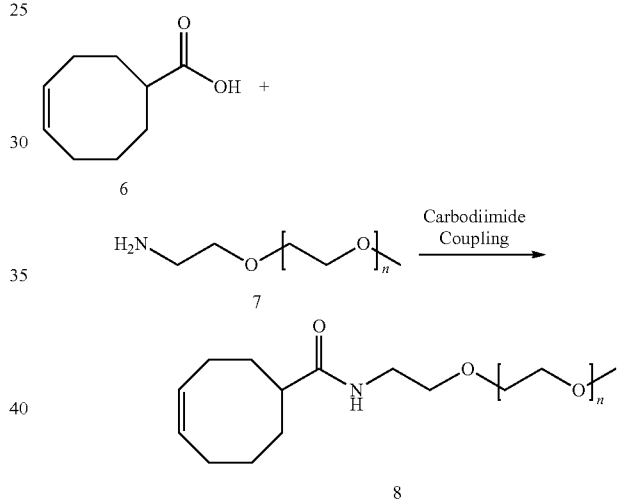

More specifically, cyclooctene acid (0.15 g, 0.99 mmol), α-methyl, ω-amine polyethylene glycol 5000 (1.00 g, 0.20 mmol), and dimethylaminopyridine (12 mg, 0.10 mmol) were combined and diluted with 6 mL of dry dichloromethane. In a separate flask, 0.21 g (1.02 mmol) dicyclohexylcarbodiimide was diluted with 4 mL dry dichloromethane and added to the reaction mixture. The solution was allowed to stir at room temperature, under nitrogen, for 12 hours. Dicycloohexylurea precipitate was filtered and the reaction mixture was washed with a 1 M HCl (aq) solution. The organic fraction was concentrated and dissolved in water followed by washing with a hexane/ethyl acetate mixture. The organic phase was washed with water an additional two times. The aqueous fractions were combined and extracted three times with chloroform. The combined organic fractions were dried over magnesium sulfate and concentrated to a viscous liquid. The concentrated product was dissolved in a minimal amount of ethyl acetate and precipitated into cold diethyl ether. The macromonomer was isolated as a white powder and dried under vacuum to yield 0.91 g (89% yield) product. $^1$H NMR (CDCl$_3$) δ 5.92 (m, 1H), 5.62 (m, 2H), 3.33-3.77 (complex, br m, 470H), 2.54 (br s, 1H), 1.32-2.42 (complex br m, 11H); $^{13}$C NMR (CDCl$_3$) δ 179.8, 131.6, 130.5, 72.7, 71.0, 70.7, 70.4, 67.8, 59.8, 45.5, 42.3, 34.2, 33.5, 25.9, 25.8, 22.8; ATR-FTIR 2882, 2741, 1654, 1467, 1360, 1341, 1280, 1241, 1146, 1100, 1060, 958, 841 cm$^{-1}$.

Example 7

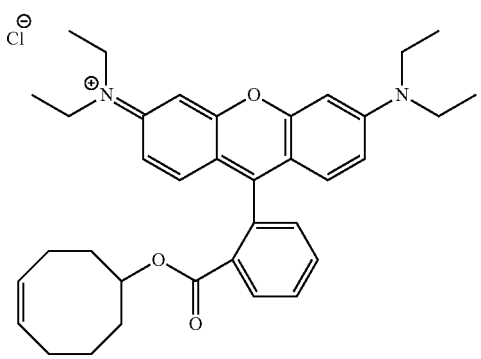

Esterification of 5-Hydroxycyclooctene with rhodamine B. 260 mg (2.09 mmol) of 5-hydroxycyclooctene, (Hillmyer, M. A.; Loredo, V. R.; Grubbs, R. H. Macromolecules 1995, 28, 6311.) 500 mg (1.04 mmol) of rhodamine B, and 1.5 mg (0.13 mmol) DMAP were stirred in dry $CH_2Cl_2$ (5 mL) under $N_{2(g)}$. In a separate flask, 0.26 g (1.25 mmol) dicyclohexyl-carbodiimide was diluted with 0.20 g (2.5 mmol) pyridine and $CH_2Cl_2$ (5 mL); this solution was then added by syringe to the reaction mixture and stirred for 24 hours at reflux under $N_{2(g)}$. The mixture was washed with 1 M $HCl_{(aq)}$ and concentrated. The product was purified by column chromatography to yield 460 mg (75%) of 1. $^1$H NMR ($CDCl_3$) δ 8.22 (m, 1H), 7.70-7.77 (m, 2H), 6.74-7.26 (m, 3H), 5.54 (m, 2H), 4.71 (m, 1H), 4.46 (m, 1H), 4.10 (m, 1H), 3.58-3.67 (m, 8H), 0.85-2.20 (br m, 22H) ppm; $^{13}$C NMR ($CDCl_3$) δ 164.6 (ester), 159.03, 157.9, 155.65, 133.3, 133.0, 131.5, 131.4, 131.0, 130.5, 130.4, 130.3, 129.8, 129.5, 129.4, 114.4, 113.7, 96.5, 96.2, 78.9, 46.2, 35.3, 34.2, 33.3, 33.0, 30.8, 29.8, 26.1, 25.8, 25.5, 25.1, 25.0, 24.7, 23.1, 22.4, 12.8 ppm; ESI mass spec. m/z 551.0; UV-Vis $\lambda_{max}$=556 nm.

Example 8

Copolymerization using rhodamine B labeled cyclooctene. PEGylated cyclooctene macromonomer (0.50 g, 0.53 mmol) (MW ca. 950), cyclooctene (58 mg, 0.52 mmol), and rhodamine B labeled cyclooctene (3.1 mg, 5.3 μmol) were weighed into a small tube and diluted with 0.2 mL dry $CH_2Cl_2$. The contents were subjected to two freeze/pump/thaw cycles and then stirred at 40° C. under $N_{2(g)}$. Grubbs' Generation II catalyst[19] (3.52 mg, 4.14 μmol) was weighed into a small vial, degassed, and diluted with dry $CH_2Cl_2$ (0.35 mL) under $N_{2(g)}$. The catalyst solution was introduced by syringe and the mixture was stirred at 40° C. until vitrified (approx. 15 minutes). The reaction was terminated using dodecyl vinyl ether, and $CH_2Cl_2$ (~1 mL) was added to improve stirring. The contents were precipitated into cold hexane, filtered, and dried under vacuum to yield the fluorescent copolymer (0.46 g, 82%). $^1$H NMR ($CDCl_3$) δ 5.34 (br, olefin 2H), 4.86 (br s, 1H), 4.22 (t, 2H), 3.5-3.7 (complex, br m), 3.36 (s, 3H), 2.61 (br m, 4H), 2.32 (br s), 1.94 (br s), 1.50 (br s), 1.26 ppm (br s); $^{13}$C NMR ($CDCl_3$) δ 172.7 (ester), 172.3 (ester), 130.0, 130.8, 129.3, 74.7, 72.3, 70.9, 69.4, 64.2, 59.4, 34.4, 33.0, 30.0, 29.7, 29.5, 28.8, 25.6 ppm. IR (NaCl plate) 2922, 2867, 1733 (ester), 1456, 1349, 1300, 1250, 1111, 1040, 968, 860 $cm^{-1}$. GPC (DMF w/0.01% LiCl vs. linear polystyrene standards) $M_n$=235,000 g/mol, $M_w$=313,000 g/mol, PDI=1.33. UV-Vis $\lambda_{max}$=556 nm.

Example 9

Numerous small molecule, oligomeric, and polymeric grafts can be attached to the polyolefin chain. These include amino acids, oligopeptides, polypeptides, poly(ethylene glycol) of a wide range molecular weight, alkyl chains of various lengths, polyesters, dendrimers of various composition and functionality (including drug-conjugated dendrimers), hyperbranched grafts, polyester-drug conjugates, monomeric and polymeric nucleic acids (i.e. DNA and RNA), methacrylate terminated PEG and polypeptides, methacrylamide terminated PEG and polypeptides, and thiol-terminated PEG. Such grafts are limited only by cycloalkene precursor, reaction therewith and copolymerization under the catalytic conditions employed.

Example 10

In particular, this example illustrates integration of the RGD-containing oligopeptide, in its protected form, into a copolymer of this invention.

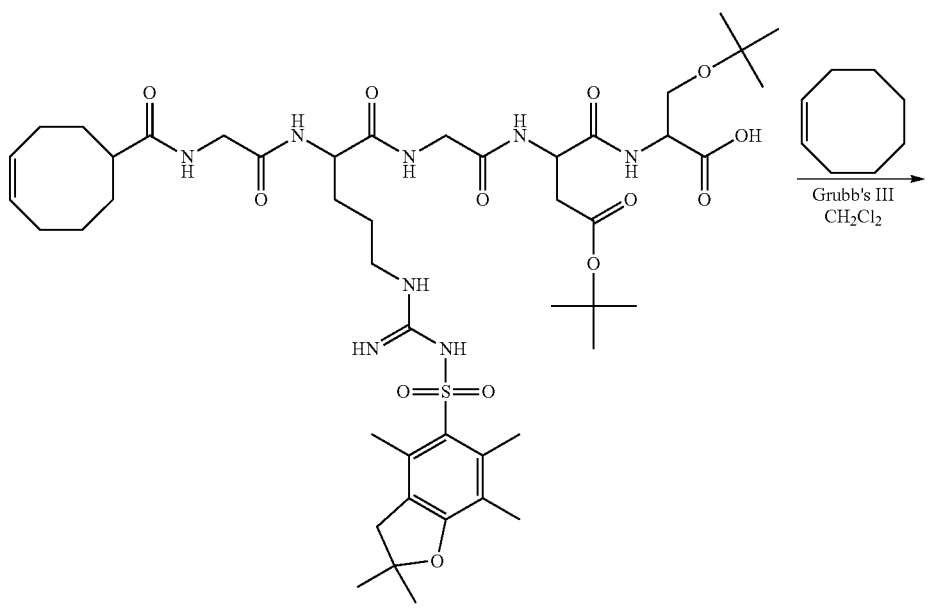

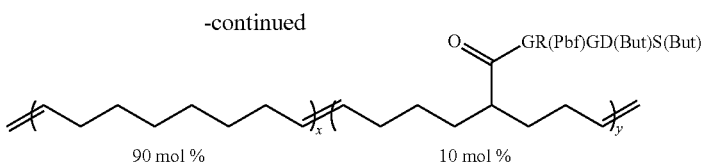

90 mol %  10 mol %

Article I. Copolymerization of Cyclooctene and Cyclooctene-GR(Pbf)GD(But)S(But)OH Monomer. A solution of cyclooctene (100 mg, 0.91 mmol) and cyclooctene-GR(Pbf)GD(But)S(But)OH monomer (100 mg, 0.101 mmol) in anhydrous $CH_2Cl_2$ (250 mL) was prepared in a reaction vial. A solution of ruthenium-based polymerization catalyst, "Grubb's Generation III catalyst" (6.2 mg, $5.06×10^{-3}$ mmol) in anhydrous $CH_2Cl_2$ (250 mL) was added to the monomer solution via syringe to give an initial monomer concentration of 2M. The initial monomer to catalyst ratio was 200/1. The vial was sealed and agitated at 40° C. for 2 min. The polymerization was allowed to cool to room temperature and ethyl vinyl ether (1 mL) was added to the vial. The reaction mixture cyclooctene crosslinker of Example 2 due to the amide linkages that connect the spacer moiety and cyclooctene endgroups: bis-cyclooctene crosslinker 10 with amide linkages formed by reaction of carboxylic acid functional cyclooctene 6 and PEG diamine 9. Again, the length of the PEG spacer can be varied over a wide range of n repeat units: n can range between 1 and about 110, but certain bis-monomers are synthesized with n between about 20 and about 50. In this range, the synthesis of bis-cyclooctene 10 is analogous to the procedure of Example 2. Bis-cyclooctene 10 is less susceptible to hydrolytic degradation than the ester versions due to the amide connectivity. This cross-linker can be used when extended hydrolytic stability of the capsules is preferred.

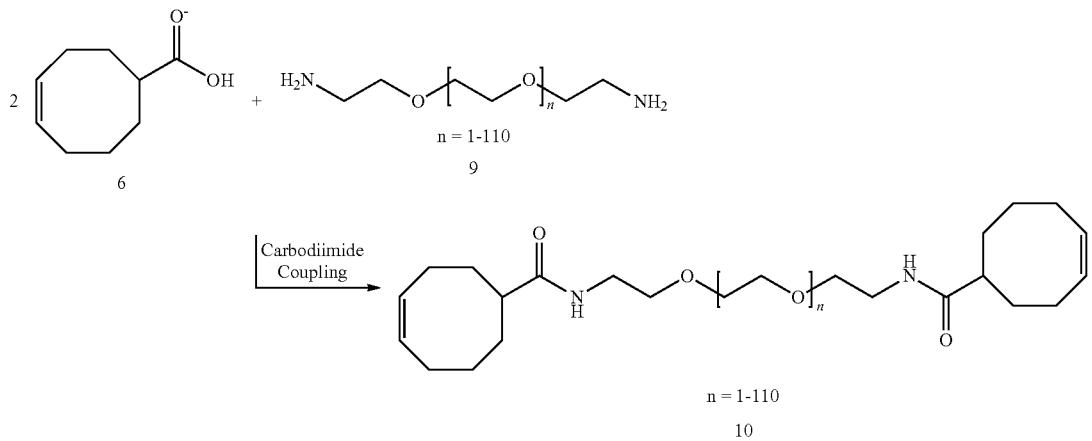

was diluted with $CH_2Cl_2$ and the polymer was isolated by precipitation into methanol (20 mL). The polymer was obtained by centrifugation, washed with methanol, and dried under vacuum to yield a yellow/white solid.

Example 11

With reference to the synthetic procedure of example 2, a variety of bis-cyclic olefin crosslinkers can be synthesized by varying the molecular weight of the PEG spacer. Alternatively, other bis-cyclic olefins containing norbornene, oxanorbornene, cycloheptene, cyclopentene, or cyclobutene moieties, prepared from the corresponding olefinic derivative, will efficiently crosslink the polymer assemblies. The choice of spacer is also not limited to PEG as a variety of other polymers such as but not limited to polypeptides and/or polyesters could be utilized to synthesize bis-cyclic olefin crosslinking agents.

Example 12

Examples 12 and 13 illustrate two bis-cyclooctene crosslinkers that have been synthesized and used to crosslinked polymer capsules by ring-opening cross metathesis. Such monomers are significantly different from the bis- More specifically, cyclooctene acid (1.2 g, 8.0 mmol), polyethylene glycol 1000 diamine (2.0 g, 2.0 mmol), and dimethylaminopyridine (0.1 g, 0.8 mmol) were combined and diluted with 20 mL of dry dichloromethane. In a separate flask, 1.2 g (6.0 mmol) dicyclohexylcarbodiimide was diluted with 10 mL dry dichloromethane followed by addition to the reaction mixture. The solution was stirred at room temperature, under nitrogen, for 12 hours. Dicycloohexylurea was filtered and the reaction mixture was washed with a 1 M HCl (aq) solution. The organic fraction was concentrated and dissolved in water followed by washing with a 50/50 Hexane/Ethyl Acetate mixture. The organic phase was washed with water an additional two times. The aqueous fractions were combined and extracted three times with chloroform. The combined organic fractions were dried over magnesium sulfate and concentrated to yield 1.1 g (42% yield) of a clear, viscous liquid. $^1$H NMR ($d_6$-DMSO) δ 7.72 (m, 2H), 5.62 (m, 4H), 3.12-3.75 (br m, 98H), 1.98-2.40 (br m, 10H), 1.25-1.78 (br m, 12H); ATR-FTIR 2882, 2741, 1654, 1467, 1360, 1341, 1280, 1241, 1146, 1100, 1060, 958, 841 $cm^{-1}$.

Example 13

The following reaction illustrates another example of a bis-cyclooctene prepared and subsequently used to crosslink amphiphilic graft copolymers. In this case, bis-cyclooctene 12 is prepared by reaction of 5-hydroxycyclooctene 5 and oligoethylene glycol dimesylate 11. The resulting bis-cyclooctene is connected by ether-linkages, and is more hydrolytically stable than amide-linked crosslinker 10 of Example 12, and much more stable than the ester-linked crosslinker of Example 2.

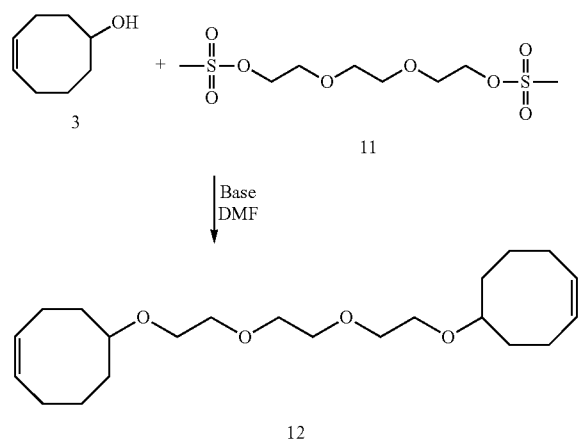

More specifically, sodium hydride (1.8 g, 73.0 mmol) was weighed into an oven dried round-bottomed flask and diluted with 150 mL anhydrous dimethylformamide (DMF). 5-hydroxycyclooctene (8.0 g, 63.4 mmol) was added as a solution in 20 mL anhydrous DMF. This mixture was allowed to stir for 1 hour followed by the addition of triethylene glycol dimesylate (7.8 g, 25.4 mmol) in 30 mL of anhydrous DMF. The reaction was stirred for 16 hr under nitrogen atmosphere. DMF and residual 5-hydroxycyclooctene removed by vacuum distillation and the residual oil was purified by column chromatography to yield 6.1 g (66% yield) of product. $^1$H NMR (CDCl$_3$) δ 5.62 (m, 4H), 3.38-3.85 (br m, 12H), 1.27-2.35 (br m, 22H); $^{13}$C NMR (CDCl$_3$) δ 130.2, 129.6, 81.1, 72.8, 71.0, 70.8, 67.8, 34.3, 33.5, 25.9, 25.8, 22.8; ATR-FTIR 3015, 2926, 2857, 1467, 1450, 1359, 1242, 1093, 1045, 988, 881, 725 cm$^{-1}$.

Example 14

Cyclooctene-methacrylates, to give crosslinking through the pendant group. Cyclic olefins containing methacrylate and methacrylamide have been synthesized and incorporated into copolymers of this invention. These functional groups allow for the rapid and efficient crosslinking of polymer capsules using free-radical, photoinitiator systems. This method permits precise control of crosslink density by varying the incorporation of the methacrylate or methacrylamide functional cyclic olefin in the copolymer. In addition, these radically crosslinkable cyclic olefins can be designed with degradable ester linkages which may be useful for the release of drugs and biological entities. Covalent crosslinking can also be carried out by incorporating thiol functional olefins or peptides containing olefins with cysteine residues. Upon oxidation, thiols react to form disulfide crosslinks which are reversible when treated with appropriate reducing agents.

Example 15

Cyclic olefins containing methacrylate and methacrylamide pendant groups have been synthesized and used for photo crosslinking. For instance, cyclooctene succinic acid ester 13 is reacted with hydroxyethyl methacrylate 14 using carbodiimide coupling conditions to yield the ester-linked, methacrylate functional monomer 15. This monomer can be copolymerized with cyclooctene and/or PEG macromonomer to yield a photocrosslinkable copolymer 16. This copolymer was used to synthesize the Doxorubicin filled capsules described in Example 16.

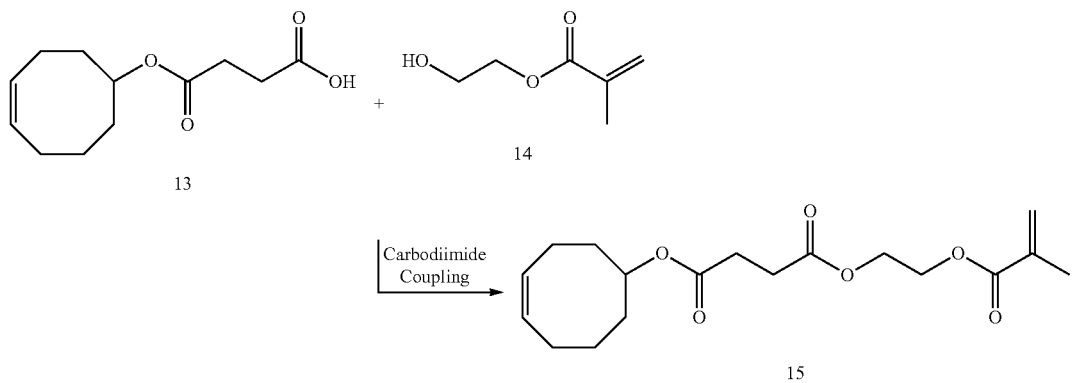

Monomer 15 can be prepared as follows. Cyclooctene acid (2.0 g, 8.8 mmol), Hydroxyethyl methacrylate (1.2 g, 9.3 mmol), and dimethylaminopyridine (80 mg, 1.0 mmol) were combined and diluted with 20 mL of dry dichloromethane. In a separate flask, pyridine (1.5 g, 19.4 mmol) and dicyclohexylcarbodiimide (2.0 g, 9.7 mmol) were diluted with 10 mL dry dichloromethane and added to the reaction mixture by syringe. The solution was allowed to stir at room temperature, under nitrogen, for 16 hours. Dicycloohexylurea was filtered and the reaction mixture was washed with a 1 M HCl (aq) solution. The organic fraction was dried over magnesium sulfate and concentrated. The product was purified by column chromatography to 2.7 g (90% yield) of product. $^1$H NMR (CDCl$_3$) δ 6.09 (s, 1H), 5.92 (m, 1H), 5.63 (m, 3H), 4.78 (m, 1H), 4.31 (s, 4H), 2.58 (m, 4H), 1.32-2.42 (complex br m, 14H); $^{13}$C NMR (CDCl$_3$) δ 172.3, 171.5, 167.2, 136.0, 129.9, 129.7, 126.2, 76.2, 62.5, 33.8, 33.7, 29.5, 29.2, 25.7, 24.9, 22.4, 18.4; ATR-FTIR 3018, 2932, 2861, 1720, 1638, 1452, 1411, 1377, 1319, 1297, 1240, 1147, 1037, 970, 941, 885, 814, 728 cm$^{-1}$.

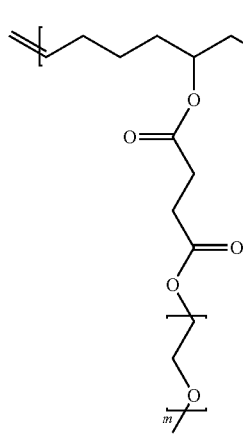

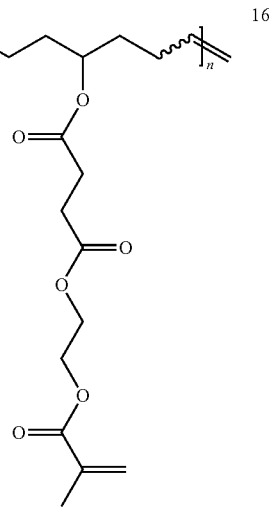

Example 16

DOX-filled capsule. 1 mg Doxorubicin was dissolved in 1 mL toluene and one drop of this solution was transferred to an aqueous solution containing 0.05 wt % polycyclooctene-g-PEG copolymer with 10 mol % methacrylate functionality. The mixture was shaken for 5 seconds after which the capsule assemblies were allowed to float to the top of the solution and the aqueous supernatant was purified of unused copolymer by repeated removal and refilling with fresh DI water. One drop of an aqueous solution containing 10 mM Eosin Y and 115 mM triethanolamine was transferred to the vial containing the doxorubicin filled capsules. The vial was shaken for 5 seconds and then placed under white light to induce the photochemical crosslinking. After 5 minutes of irradiation, the solution was purified by removing the aqueous supernatant followed by introduction of fresh DI water (3×). DOX filled capsules were observed by fluorescence confocal laser scanning microscopy.

Example 17

Free radical cross-linking of copolymers such as those shown in Example 15 are susceptible to degradation by hydrolysis of the succinic acid esters. However, such structure offers a mechanism for controlled release of the capsule contents over a tunable time frame. In some cases, it is desirable for the capsule contents to be released over much longer times, with hydrolysis of crosslinks minimized. For this reason, methacrylamide functionalized cyclooctene 19 was prepared by the carbodiimide coupling of 5-amino cyclooctene 17 and methacrylic acid 18, as illustrated below. The methacrylamide pendant group has been used to photocrosslink polymer capsules, and the amide connectivity provides dramatically improved hydrolytic stability and slower degradation.

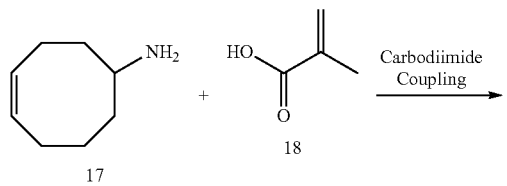

-continued

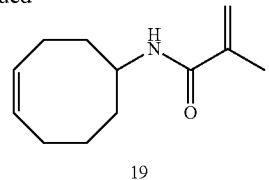

Example 18

Coumarin-filled capsule. 5 mg Coumarin 153, 25 mg bis-cyclooctene crosslinker, and 2.5 mg of polycyclooctene-g-PEG ($M_n$ 55 K g/mol) were dissolved in 1 g of toluene. Approximately 1 mg of Grubbs' Generation II catalyst was added to this mixture and a small aliquot was transferred to vial containing 4 mL of DI water. The heterogeneous mixture was shaken by hand for 5 seconds followed by shaking at 500 rpm for 15 minutes in laboratory shaker. The aqueous phase was purified by repeated removal and refilling with fresh DI water. Coumarin 153 filled capsules were shown by fluorescence confocal laser scanning.

Example 19

Various examples, herein, describe covalent crosslinking of polymer capsules by a ring-opening cross metathesis reaction with the unsaturated polymer assemblies, a bis-cyclooctene crosslinker, and the widely-known Grubbs' Generation II catalyst. It should also be noted that the ring-opening cross-metathesis cross-linking reaction can be carried out using any of the three ruthenium benzylidene catalysts or variations thereof commonly referred to as Grubbs' Generation I-III catalysts, below. Such catalysts (with ligand and metal center variations thereof) are known in the art, and are commercially-available or can be prepared according to literature references. When using catalysts of this sort for interfacial cross-linking, the best results were obtained by the use of Grubbs' Generation III catalyst. Any such catalyst can be used as described herein or with straightforward modifications of such synthetic techniques, depending upon solvent or monomer choice, as would be understood by those skilled in the art. Likewise, other catalysts for ring-opening metathesis polymerizations, including Mo- and Os-based compounds, can be used.

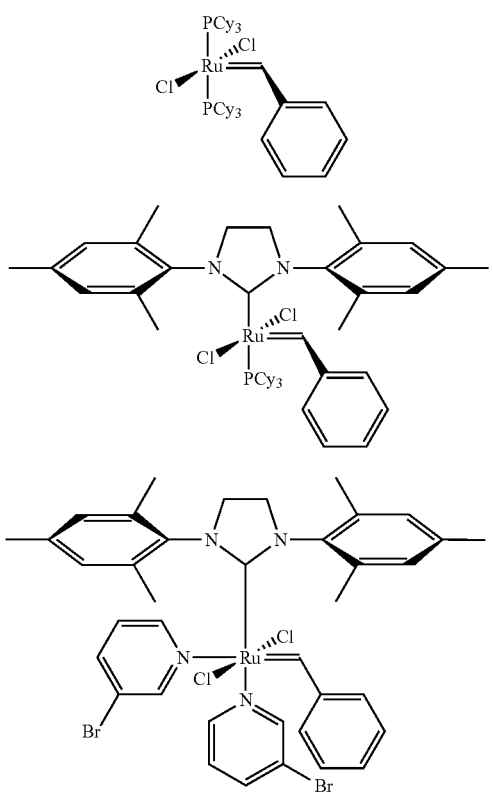

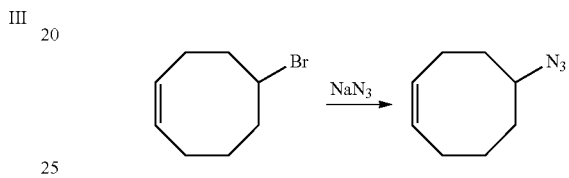

Example 20a

Figure 4:
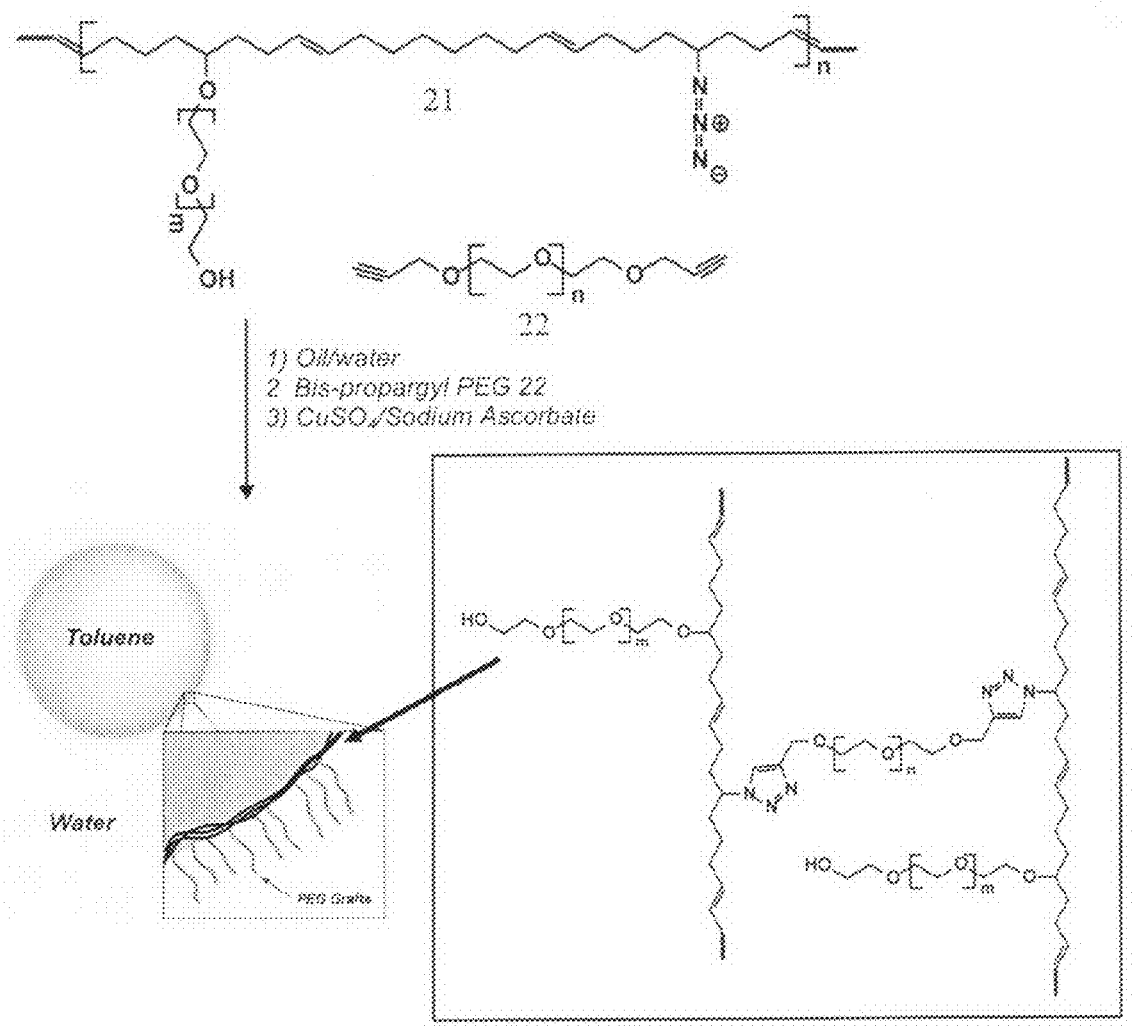
FIG. 4. With reference to examples 20a-e, crosslinking of an azide-functionalized copolymer, in accordance with this invention.

This example illustrates the synthesis of a PEG-grafted polyolefin containing a pendant azide functionality. This new polymer was prepared by the synthesis and polymerization of a novel azide functionalized cyclic olefin 20. The copolymer has been synthesized with and without unsubstituted cyclooctene, and has been shown to form polymer capsules using methods described elsewhere, herein. FIG. 4 is a schematic representation of the interfacial crosslinking of azide-functional copolymer 21 using diacetylene crosslinker 22. Although 22 is shown with a PEG spacer, the type of spacer can be varied to include, without limitation, polypeptide, polyester, and other spacers. Most often, the crosslinking is carried out using a diacetylene with a PEG spacer (n=about 5-about 50). Reaction of the respective azide and acetylene groups proceeds via (3+2) cycloaddition to afford triazole moieties, which can effectively crosslink the azide-functionalized amphiphilic graft copolymer 21 at the fluid (e.g., oil/water) interface. Copper sulfate and sodium ascorbate can be included in the aqueous phase to increase the rate of crosslinking.

Example 20b 5-bromocyclooctene (13.5 g, 71.4 mmol) and sodium azide (23.2 g, 357.0 mmol) combined in 150 mL of dimethylsulfoxide (DMSO). The reaction was heated to 110° C. and stirred for 5 hr. After cooling to room temperature, deionized water (150 mL) was added to the mixture and the product was extracted two times with diethyl ether. The combined organic fractions were dried over magnesium sulfate and concentrated. The product was purified by column chromatography and yielded 8.1 g (75% yield) of product. $^1$H NMR (CDCl$_3$) δ 5.62 (m, 2H), 3.46 (m, 1H), 1.32-2.39 (complex br m, 11H); $^{13}$C NMR (CDCl$_3$) δ 129.9, 129.7, 62.2, 32.9, 32.0, 26.6, 26.0, 23.4; ATR-FTIR 3019, 2930, 2858, 2086, 1466, 1446, 1368, 1346, 1318, 1294, 1251, 1219, 991, 926, 882, 726 cm$^{-1}$.

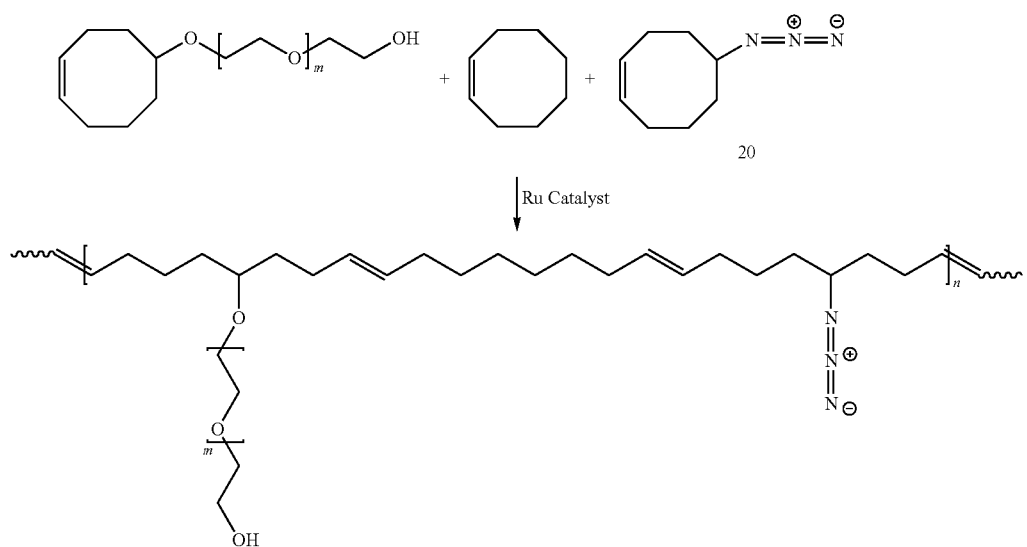

Example 20c

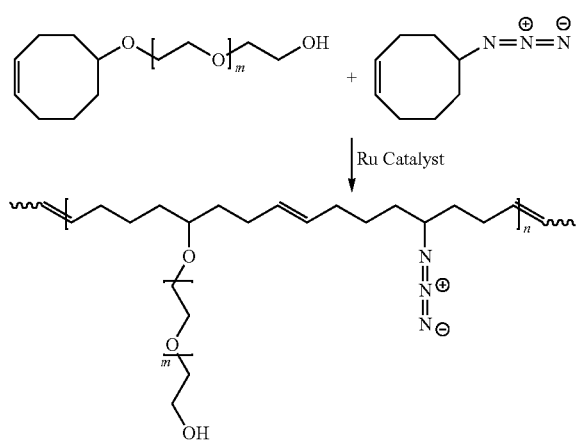

Optionally, a polymer with a pendant azide group can be prepared without cyclooctene monomer, as follows. PEG 2200 (m~50) macromonomer (0.50 g, 0.22 mmol) and 5-azocyclooctene (0.08 g, 0.51 mmol) were combined in a reaction tube. 0.6 mL of dry dichloromethane was added to dilute the mixture. In a separate vial, 12.4 mg (14.6 µmol) Grubbs' Generation II catalyst was diluted with 0.2 mL dry dichloromethane. Both the reaction mixture and catalyst solution were subjected to two freeze/pump/thaw cycles followed by addition of the catalyst solution to the reaction mixture. The mixture was stirred at 40° C. for 1 hr. Approximately 1 mL of dodecyl vinyl ether was added to terminate the polymerization and dichloromethane was added to dilute the polymer solution. The product was precipitated into cold hexane, isolated, and dried under vacuum to yield 0.41 g (71%) of polymer. $^1$H NMR (CDCl$_3$) δ 5.37 (m), 3.38-3.85 (br m), 3.23 (br m), 2.92 (m), 2.40 (br s), 1.99, (br m), 1.27-1.60 (br m); $^{13}$C NMR (CDCl$_3$) δ 130.2, 129.4, 79.4, 72.5, 70.8, 70.5, 70.3, 68.0, 62.4, 61.7, 34.0, 33.5, 32.3, 29.2, 28.4, 27.0; ATR-FTIR 2863, 2096, 1466, 1343, 1280, 1242, 1103, 962, 842, 727 cm$^{-1}$.

Example 20d

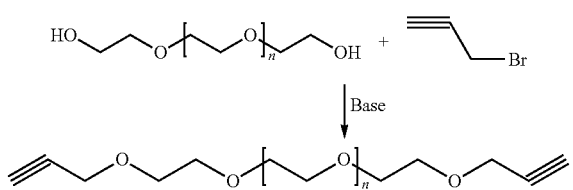

A diacetylene, for cycloaddition with azide 20 can be prepared as follows. Potassium tert-butoxide (5.9 g, 52.5 mmol) was weighed into an oven dried round-bottomed flask and diluted with 80 mL dry THF. The mixture was cooled using an ice-water bath and polyethylene glycol 300 (7.0 g, 23.3 mmol) was added as a solution in 20 mL dry THF. The solution was allowed to stir for 30 min followed by addition of 15.6 mL (104.9 mmol) propargyl bromide (80 wt % in toluene) by syringe. The reaction was allowed to stir for 1 hr at 0° C. and then at room temperature for an addition 12 hr. The mixture was diluted with brine and extracted three times with ethyl acetate. The combined organic fractions were dried over magnesium sulfate, concentrated, and further purified by column chromatography to afford 5.1 g (42%) of a pale yellow liquid. $^1$H NMR (CDCl$_3$) δ 4.12 (d, 4H), 3.58-3.65 (br m, 28H), 2.39 (t, 2H); $^{13}$C NMR (CDCl$_3$) δ 79.6, 74.7, 70.6, 70.4, 69.1, 58.4; ATR-FTIR 3245, 2866, 1458, 1349, 1291, 1248, 1092, 1032, 947, 919, 843 cm$^{-1}$.

Capsule Preparation

Example 20e

Crosslinking via (3+2 Cycloaddition) can be achieved as follows. 5 mg of azide-functional polycyclooctene-g-PEG copolymer and 100 mg of polyethylene glycol diacetylene were dissolved in 1 mL of toluene. In a separate vial, 25 mg of copper sulfate and 25 mg sodium ascorbate were dissolved in 12 mL of deionized water. Three drops of the organic solution was transferred to the water/catalyst solution and the vial was shaken for 10-15 seconds followed by gentle stirring by hand. After approx 15 min, the capsules were isolated by ultrafiltration or fractionation in separatory funnel.

Example 21

Aqueous phase encapsulation. The previous examples are of cases where capsules are formed with oil on the inside and water on the outside. The inverse case can be prepared, where water is on the inside and the organic phase is outside. For example, 25 mg bis-cyclooctene crosslinker and 2.5 mg of polycyclooctene-g-PEG (M$_n$ 55 K g/mol) were dissolved in 1 g of water and a small aliquot was transferred to vial containing 4 mL of toluene. After shaking the mixture for 5 seconds, approximately 5 mg of Grubbs' Generation II catalyst was added to the mixture followed by additional shaking at 500 rpm for 15 minutes in a laboratory shaker. The catalyst was removed by extraction of the toluene supernatant followed by introduction of toluene (3×) to give the crosslinked capsule.

Example 22

Regardless of phase configuration or identity of any particular phase component, any of the polymers described herein can be interfacially assembled as provided in examples 16, 18 and/or 21. Likewise, as would be understood by those in the art, one or more monomeric components can be provided with or introduced to one phase component, with an appropriate polymerization catalyst added before or after introduction of a second phase component. Interfacial assembly proceeds, accordingly.

While the principles of this invention have been described in connection with specific embodiments, it should be understood clearly that these descriptions are added only by way of example and are not intended to limit, in any way, the scope of this invention. For instance, the present invention can be applied more specifically to the interfacial assembly of graft copolymers other than those described herein, such polymers limited only by structure and composition of the polymeric components and their respective, corresponding phase interaction or association. Likewise, in addition to the agents described herein, the phase components of such a system can comprise various other compounds or materials, including but not limited to agricultural pesticides, perfumes and detergents, for encapsulation by the assembled polymers.

We claim:

1. A formulation capsule comprising a graft co-polymer of cyclooctene and poly(alkylene oxide)-substituted cyclooctene.

2. The formulation capsule of claim 1 wherein said graft copolymer is the ring opening metathesis polymerization product of cyclooctene and a poly(alkylene oxide)-substituted cyclooctene.

3. The formulation capsule of claim 1 wherein said graft co-polymer is cross-linked with poly(alkylene oxide) moieties.

4. The formulation capsule of claim 3 wherein said cross-linker comprises a linker moiety selected from acrylate, methacrylate, acrylamide and triazole moieties, said triazole moiety the cycloaddition product of an azide and an acetylene.

5. The formulation capsule of claim 1 wherein said co-polymer comprises a bis-cyclooctene monomer.

6. The formulation capsule of claim 1 encapsulating an agent selected from therapeutic, analytic and diagnostic agents.

7. A capsule comprising a ring opening metathesis polymerization polymer comprising a first cycloalkene monomeric component, said component comprising a pendent substituent, said capsule interfacially assembled at a phase component interface of a fluid bi-phasic system.

8. The capsule of claim 7 wherein said substituent comprises a poly(alkylene oxide) component.

9. The capsule of claim 7 wherein said first cycloalkene monomeric component comprises cyclooctene.

10. The capsule of claim 7 comprising a second cycloalkene monomeric component.

11. The capsule of claim 10 wherein said second cycloalkene monomeric component comprises a pendent substituent.

12. The capsule of claim 10 wherein at least one of said first and second cycloalkene monomeric components comprises a substituent cross-linking said components.

13. The capsule of claim 10 wherein said second cycloalkene monomeric component comprises a bis-cycloalkene component.

14. The capsule of claim 10 comprising a third cycloalkene monomeric component comprising a pendent functionality for cross-linking with another said third monomeric component.

15. The capsule of claim 7 wherein a said fluid phase component is within said capsule.

16. The capsule of claim 15 wherein an agent is partitioned in said fluid phase component.

17. The capsule of claim 16 wherein said agent selected from therapeutic, analytic and diagnostic agents.

18. The capsule of claim 7 wherein said first monomeric component comprises cyclooctene, and said pendent substituent comprises poly(ethylene oxide).

19. The capsule of claim 18 comprising at least one of a cyclooctene monomeric component, a bis-cyclooctene monomeric component comprising a poly(alkylene oxide) cross-linking moiety, and a cyclooctene monomeric component comprising a pendent functionality for cross-linking.

20. The capsule of claim 19 wherein said pendent functionality is selected from methacrylate, methacrylamide, acetylene and azide.

21. A capsule comprising a ring opening metathesis polymerization co-polymer comprising at least two cycloalkene monomeric components; and a material within said capsule.

22. The capsule of claim 21 wherein at least one of said monomeric components comprises a pendent substituent.

23. The capsule of claim 22 wherein said substituent comprises a poly(alkylene oxide) component.

24. The capsule of claim 21 wherein said co-polymer is cross-linked.

25. The capsule of claim 24 wherein said cross-link comprises a linker moiety selected from acrylate, methacrylate and triazole moieties, said triazole moiety the cycloaddition product of an azide and an acetylene.

26. The capsule of claim 21 comprising at least two of a cyclooctene monomeric component, a cyclooctene monomeric component comprising a poly(alkylene oxide) substituent, a bis-cyclooctene monomeric component comprising a poly(alkylene oxide) cross-linking moiety, and a cyclooctene monomeric component comprising a pendent functionality for cross-linking.

27. The capsule of claim 21 wherein said material is selected from therapeutic, analytic and diagnostic agents.

* * * * *